(12) United States Patent
Duffy

(10) Patent No.: US 10,154,905 B2
(45) Date of Patent: Dec. 18, 2018

(54) SYSTEM AND METHOD FOR DEFLECTING A DELIVERY CATHETER

(71) Applicant: Medtronic Vascular, Inc., Santa Rosa, CA (US)

(72) Inventor: Niall Duffy, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 528 days.

(21) Appl. No.: 14/820,633

(22) Filed: Aug. 7, 2015

(65) Prior Publication Data

US 2017/0035567 A1    Feb. 9, 2017

(51) Int. Cl.
| | |
|---|---|
| *A61F 2/24* | (2006.01) |
| *A61F 2/966* | (2013.01) |
| *A61M 25/00* | (2006.01) |
| *A61M 25/01* | (2006.01) |

(52) U.S. Cl.
CPC ............ *A61F 2/2436* (2013.01); *A61F 2/966* (2013.01); *A61M 25/008* (2013.01); *A61M 25/0052* (2013.01); *A61M 25/0144* (2013.01); *A61F 2250/0018* (2013.01); *A61F 2250/0029* (2013.01); *A61M 2025/015* (2013.01)

(58) Field of Classification Search
CPC ............... A61F 2/2436; A61F 2/966; A61F 2250/0018; A61F 2250/0029; A61M 25/008; A61M 25/0144; A61M 25/0052; A61M 2025/015
See application file for complete search history.

(56) References Cited

U.S. PATENT DOCUMENTS

| | | | | |
|---|---|---|---|---|
| 4,940,062 A | * | 7/1990 | Hampton | A61M 25/09033 600/434 |
| 5,383,923 A | * | 1/1995 | Webster, Jr. | A61B 5/0422 607/125 |
| 5,395,328 A | * | 3/1995 | Ockuly | A61M 25/0144 600/585 |
| 5,396,902 A | * | 3/1995 | Brennen | A61M 25/0136 600/585 |
| 5,397,304 A | * | 3/1995 | Truckai | A61M 25/0138 604/528 |
| 5,480,382 A | * | 1/1996 | Hammerslag | A61M 25/0053 600/585 |
| 5,487,757 A | * | 1/1996 | Truckai | A61B 18/1492 604/264 |
| 5,545,200 A | * | 8/1996 | West | A61B 18/1492 606/29 |

(Continued)

FOREIGN PATENT DOCUMENTS

WO    WO2012/096687    7/2012

OTHER PUBLICATIONS

PCT/US2016/042346, The International Search Report and the Written Opinion of the International Searching Authority, dated Oct. 19, 2016.

*Primary Examiner* — Son Dang
(74) *Attorney, Agent, or Firm* — Medler Ferro Woodhouse & Mills PLLC

(57) ABSTRACT

Distal tips for use with delivery catheters are disclosed that are configured to facilitate deflection of the catheters as they are advanced through the vasculature to a desired treatment site. Distal tips so configured realize one or more of the objectives of safer, more accurate steering of the catheter through the vasculature.

6 Claims, 14 Drawing Sheets

(56) References Cited

U.S. PATENT DOCUMENTS

| | | | | |
|---|---|---|---|---|
| 5,904,667 A * | 5/1999 | Falwell | A61M 25/0147 | 600/146 |
| 5,944,690 A * | 8/1999 | Falwell | A61M 25/0147 | 600/146 |
| 6,120,476 A * | 9/2000 | Fung | A61B 18/1492 | 604/528 |
| 6,146,338 A * | 11/2000 | Gardeski | A61M 25/0138 | 600/585 |
| 6,468,260 B1 * | 10/2002 | Bumbalough | A61M 25/0136 | 600/434 |
| 6,579,278 B1 * | 6/2003 | Bencini | A61M 25/0144 | 600/585 |
| 6,585,717 B1 * | 7/2003 | Wittenberger | A61M 25/0138 | 604/523 |
| 6,607,496 B1 * | 8/2003 | Poor | A61M 25/0012 | 600/585 |
| 7,004,938 B2 * | 2/2006 | Ormsby | A61B 18/1492 | 606/33 |
| 7,056,314 B1 * | 6/2006 | Florio | A61M 25/0136 | 604/528 |
| 7,776,062 B2 * | 8/2010 | Besselink | A61F 2/013 | 600/184 |
| 7,811,277 B2 * | 10/2010 | Boulais | A61B 1/0052 | 604/528 |
| 9,636,138 B2 * | 5/2017 | Schneider | A61B 17/320758 | |
| 9,775,963 B2 * | 10/2017 | Miller | A61M 25/0012 | |
| 9,795,765 B2 * | 10/2017 | Romoscanu | A61M 25/0013 | |
| 9,808,311 B2 * | 11/2017 | Wang | A61B 18/1492 | |
| 9,833,595 B2 * | 12/2017 | Gonzalez | A61B 1/0052 | |
| 2001/0037084 A1 * | 11/2001 | Nardeo | A61M 25/008 | 604/95.04 |
| 2001/0039418 A1 * | 11/2001 | Schaer | A61B 18/1492 | 606/41 |
| 2002/0165534 A1 * | 11/2002 | Hayzelden | A61M 25/0144 | 606/41 |
| 2003/0130712 A1 * | 7/2003 | Smits | A61M 25/0138 | 607/116 |
| 2006/0142732 A1 * | 6/2006 | Karmarkar | A61M 25/0138 | 604/508 |
| 2006/0265056 A1 | 11/2006 | Nguyen et al. | | |
| 2007/0066878 A1 * | 3/2007 | Worley | A61B 18/1492 | 600/374 |
| 2007/0156116 A1 * | 7/2007 | Gonzalez | A61B 1/0052 | 604/528 |
| 2007/0239266 A1 | 10/2007 | Birdsall | | |
| 2007/0239269 A1 | 10/2007 | Dolan et al. | | |
| 2008/0071361 A1 | 3/2008 | Tuval et al. | | |
| 2008/0161775 A1 * | 7/2008 | Potter | A61M 25/0041 | 604/525 |
| 2009/0163917 A1 * | 6/2009 | Potter | A61B 18/1492 | 606/41 |
| 2009/0264863 A1 * | 10/2009 | Bloom | A61M 25/0054 | 604/524 |
| 2010/0217185 A1 * | 8/2010 | Terliuc | A61B 1/018 | 604/96.01 |
| 2010/0280316 A1 * | 11/2010 | Dietz | A61B 8/12 | 600/109 |
| 2011/0098804 A1 * | 4/2011 | Yeung | A61F 2/2412 | 623/2.1 |
| 2011/0112476 A1 * | 5/2011 | Kauphusman | A61M 25/0012 | 604/95.04 |
| 2011/0112563 A1 * | 5/2011 | To | A61B 17/320783 | 606/159 |
| 2011/0207999 A1 * | 8/2011 | Torisawa | A61B 1/00078 | 600/114 |
| 2011/0251681 A1 * | 10/2011 | Shipley | A61F 2/2436 | 623/2.11 |
| 2011/0251682 A1 * | 10/2011 | Murray, III | A61F 2/2436 | 623/2.11 |
| 2012/0277730 A1 * | 11/2012 | Salahieh | A61B 1/00135 | 604/527 |
| 2012/0305441 A1 | 12/2012 | Murray et al. | | |
| 2012/0310332 A1 | 12/2012 | Murray et al. | | |
| 2013/0096553 A1 * | 4/2013 | Hill | A61N 1/05 | 606/41 |
| 2013/0297012 A1 * | 11/2013 | Willard | A61F 2/2436 | 623/2.11 |
| 2014/0135895 A1 | 5/2014 | Andress et al. | | |
| 2014/0148889 A1 * | 5/2014 | Deshmukh | A61F 2/962 | 623/1.11 |
| 2014/0243953 A1 | 8/2014 | Stante et al. | | |
| 2015/0352327 A1 * | 12/2015 | Helgeson | A61M 25/0147 | 604/95.04 |
| 2017/0113020 A1 * | 4/2017 | Hebert | A61M 25/0138 | |
| 2017/0113021 A1 * | 4/2017 | Hebert | A61M 25/0138 | |
| 2017/0189646 A1 * | 7/2017 | Hebert | A61M 25/0138 | |
| 2017/0232234 A1 * | 8/2017 | McDaniel | A61M 25/0138 | 600/374 |
| 2017/0296787 A1 * | 10/2017 | Potter | A61B 18/1492 | |

* cited by examiner

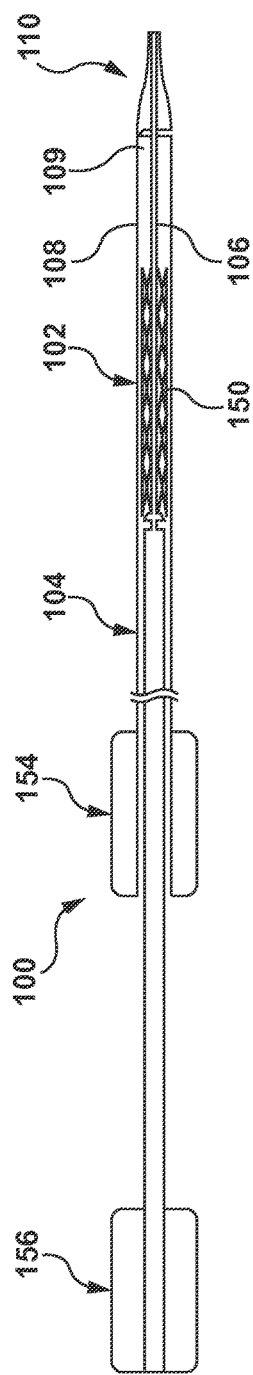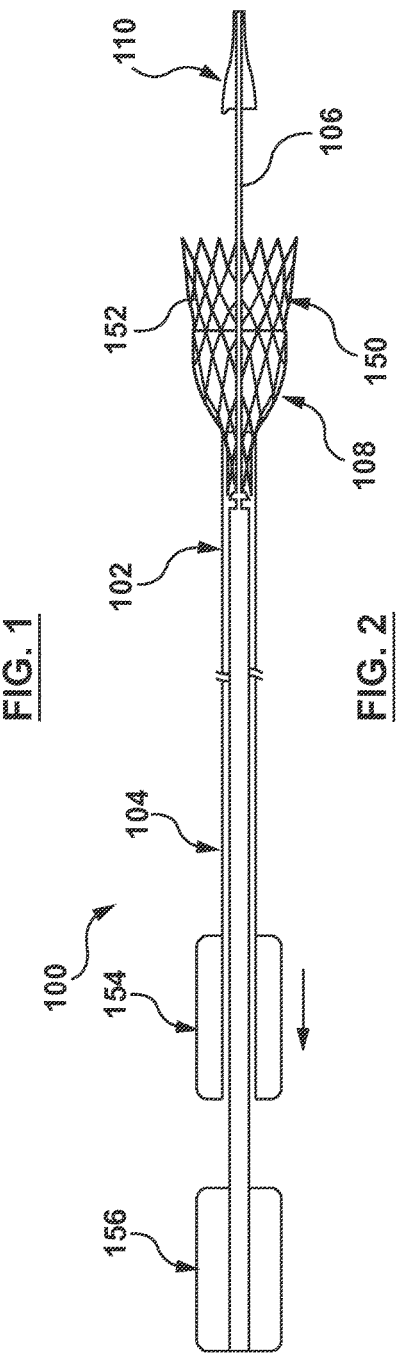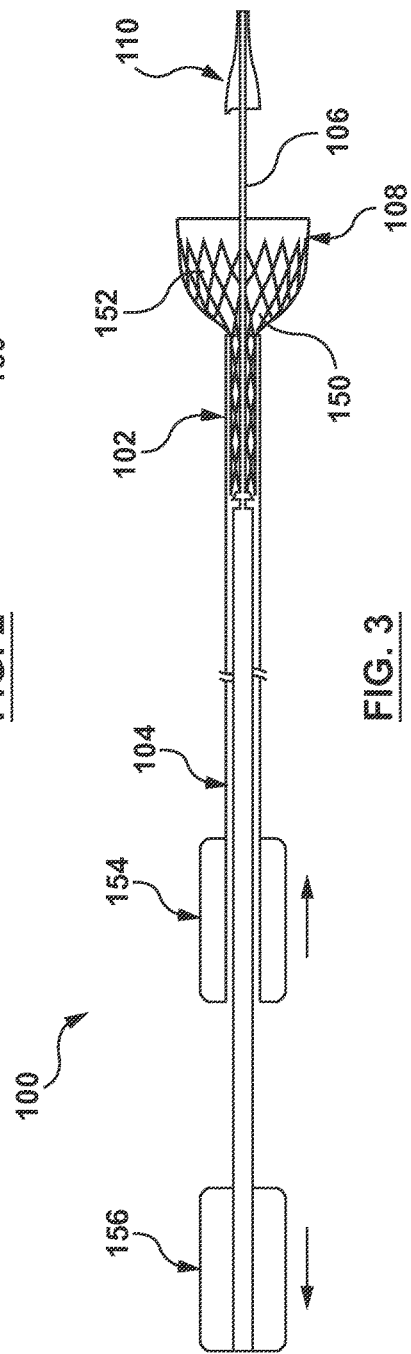
FIG. 1
FIG. 2
FIG. 3

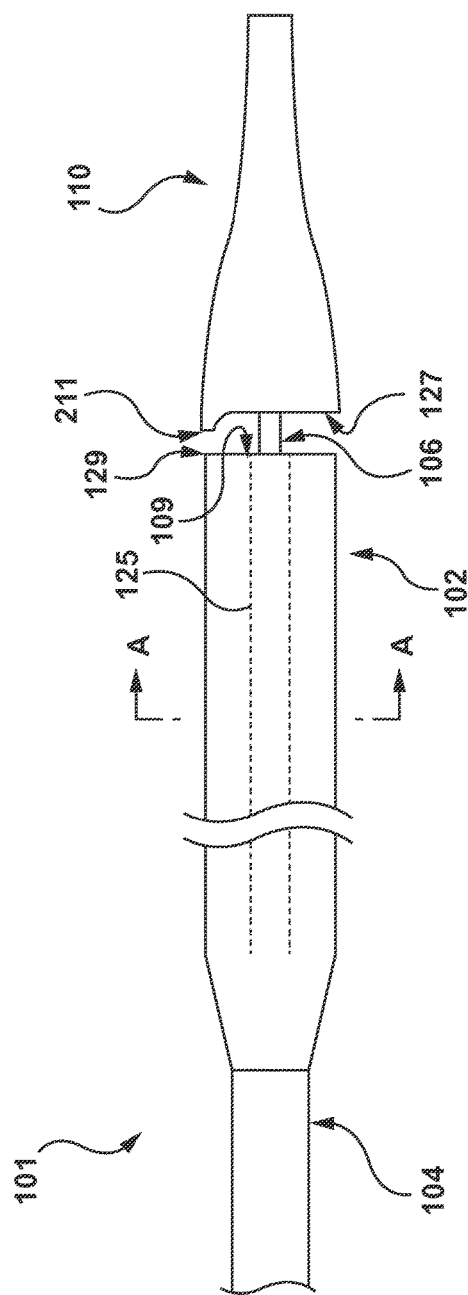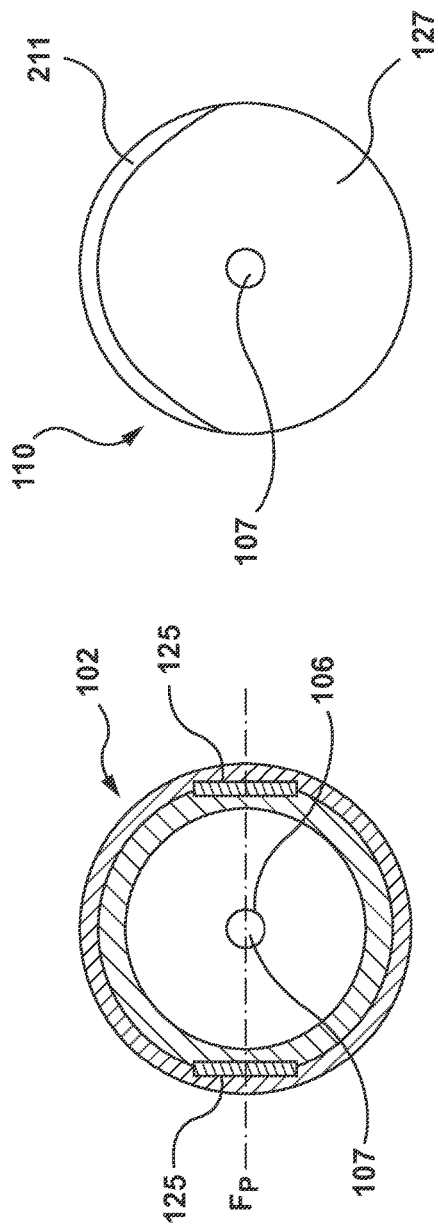
FIG. 6
FIG. 6A
FIG. 6B

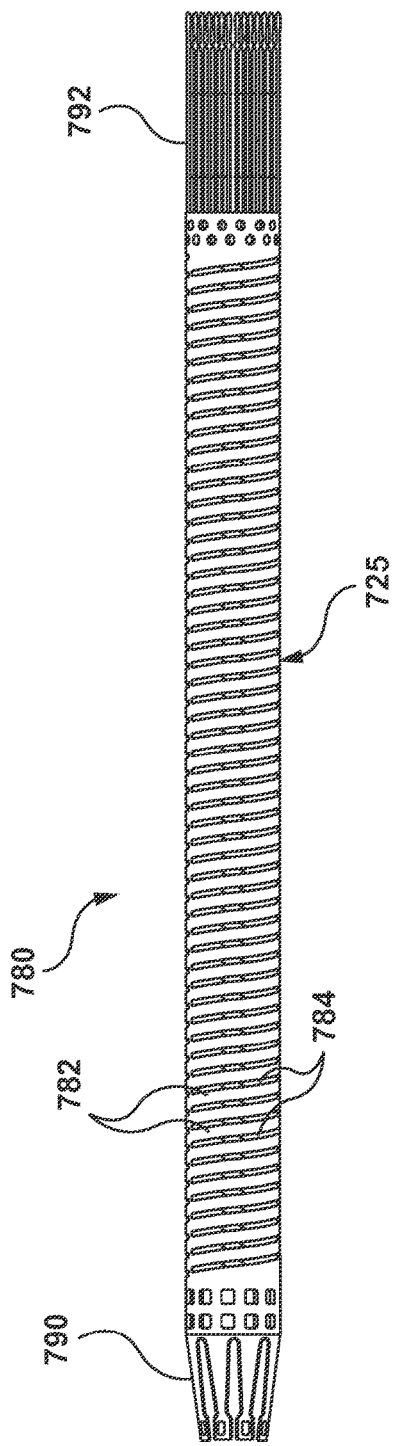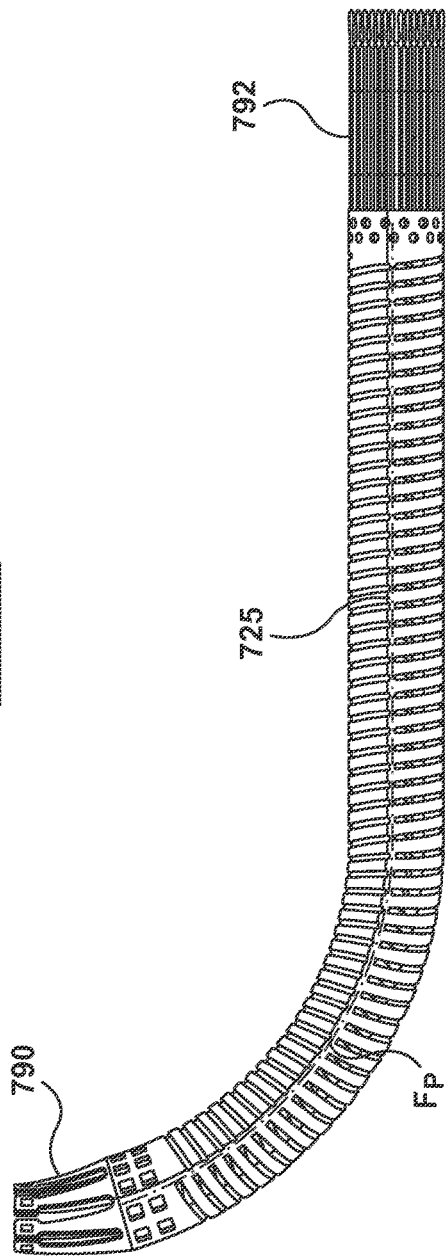
FIG. 7A
FIG. 7B

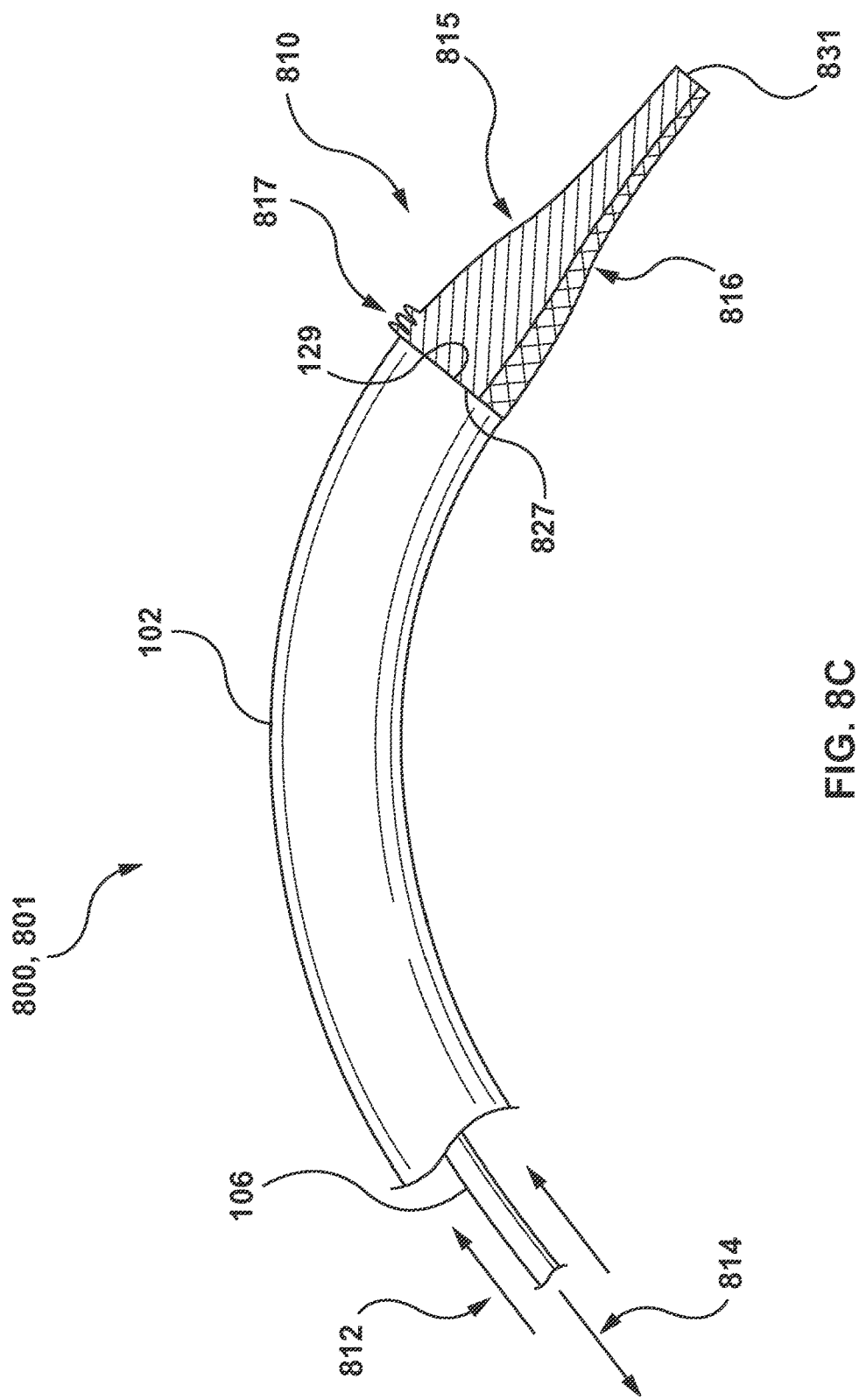

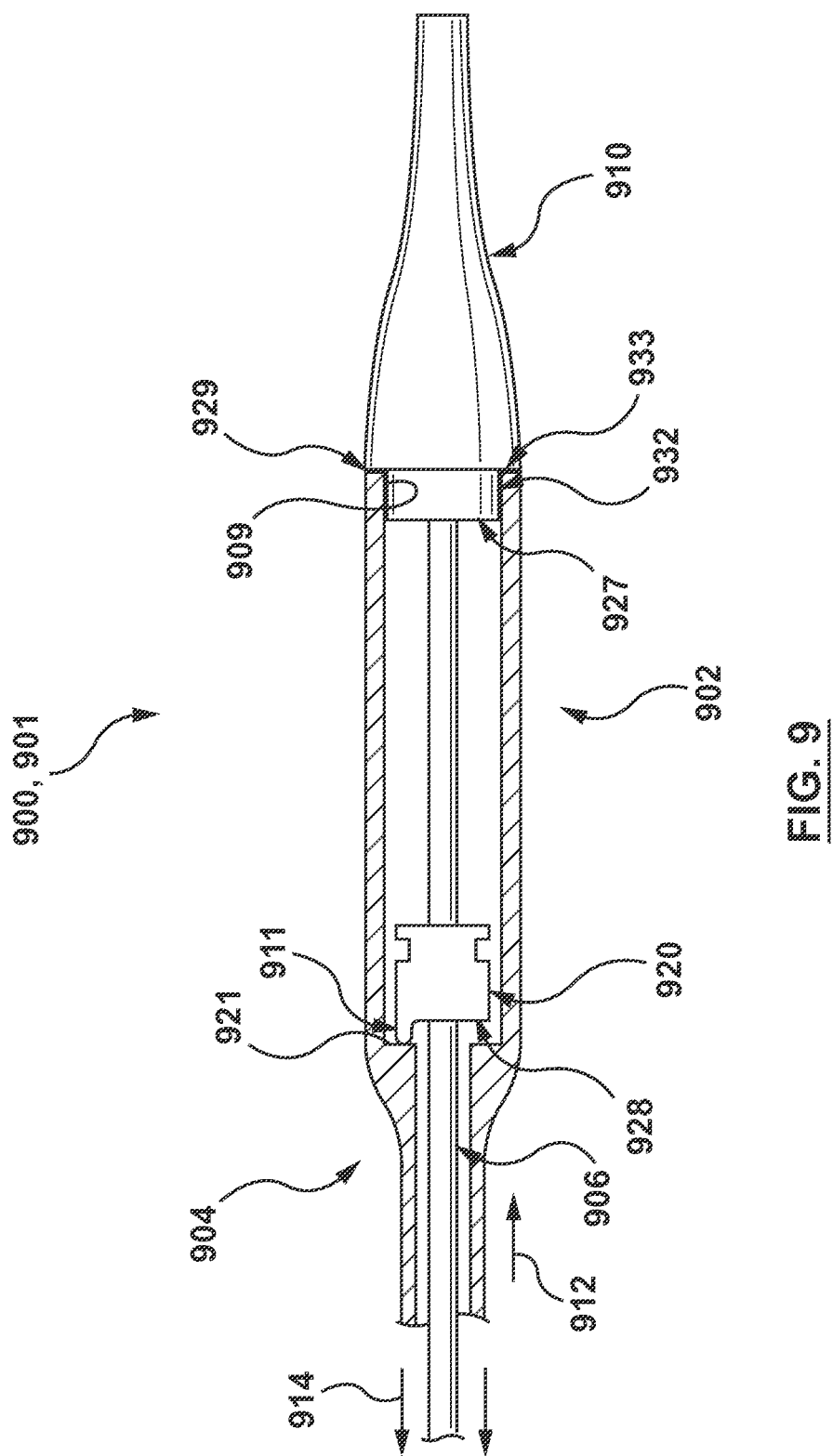

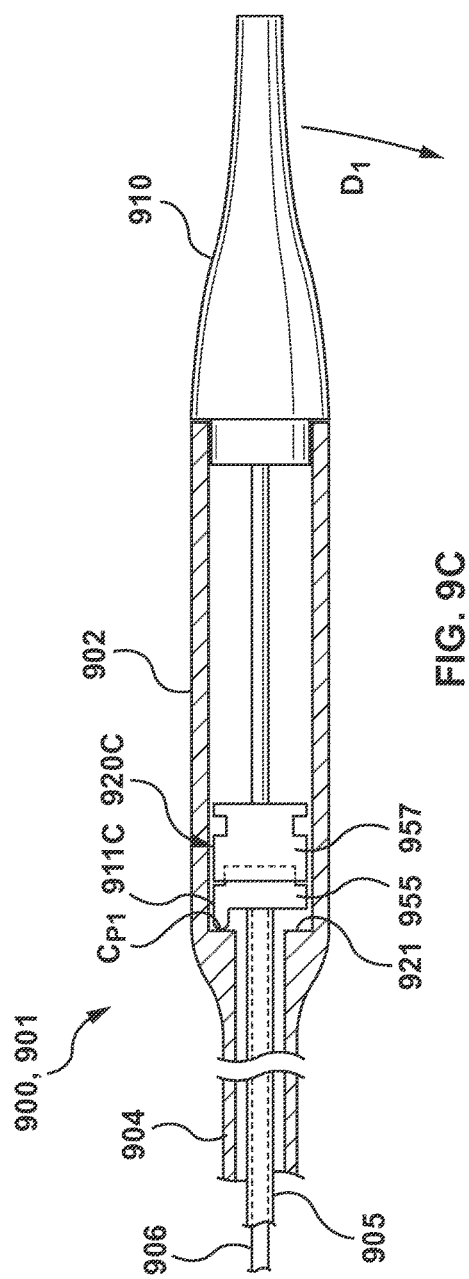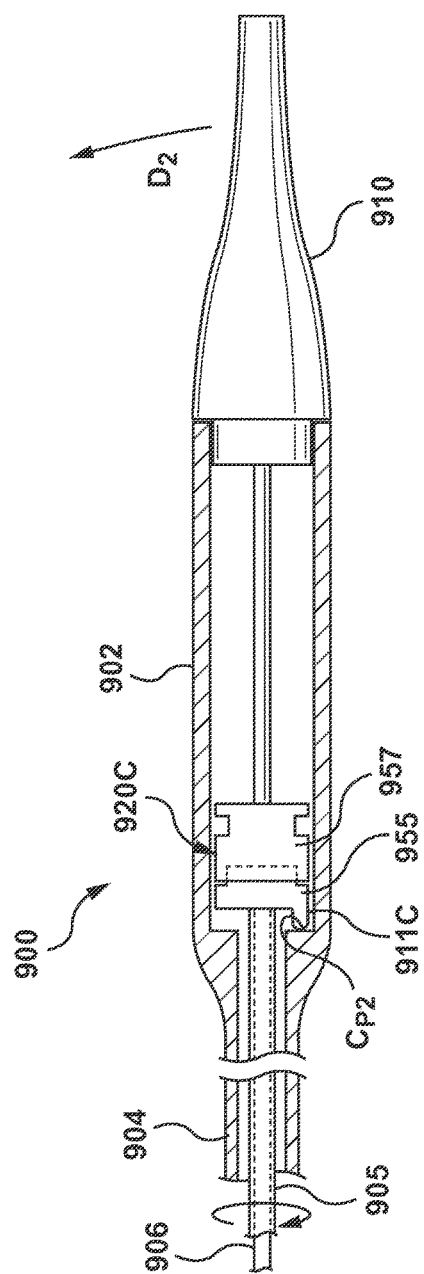

SYSTEM AND METHOD FOR DEFLECTING A DELIVERY CATHETER

FIELD OF THE INVENTION

The invention relates to a delivery catheter, such as a delivery catheter for delivering a prosthesis, and more particularly is directed to a distal tip of the delivery catheter.

BACKGROUND OF THE INVENTION

Diseased or otherwise deficient heart valves can be repaired or replaced with an implanted prosthetic heart valve. The terms "repair" and "replace" are used interchangeably throughout the specification, and a reference to "repair" of a defective native heart valve is inclusive of a prosthetic heart valve that renders the native leaflets non-functional, or that leaves the native leaflets intact and functional. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be restored (e.g., the aortic valve annulus). Although transcatheter techniques have attained widespread acceptance with respect to the delivery of conventional stents to restore vessel patency, only mixed results have been realized with percutaneous delivery of the more complex prosthetic heart valve.

Various types and configurations of prosthetic heart valves are available or have been proposed for percutaneous transcatheter valve replacement procedures. In general, prosthetic heart valve designs attempt to replicate the functions of the native heart valve being replaced and thus will include valve leaflet-like structures mounted in some manner within an expandable stent frame, which in some instances is made of a shape memory material and construction. With such shape memory or self-expanding stent frames, the prosthetic heart valve is crimped to a desired size and held in a compressed delivery configuration within a retaining sheath, sleeve or capsule of a delivery catheter, for example, for delivery to a treatment site within the heart. In certain percutaneous transcatheter valve replacement procedures, the delivery catheter is introduced into a vessel, for example, the femoral artery or the brachial artery and tracked through the vasculature to the heart. Once the delivery catheter and more particularly the prosthetic heart valve are properly positioned with the native valve to be replaced, the retaining sheath, sleeve or capsule is retracted from the prosthetic heart valve to permit the stent frame to return to its expanded diameter for implantation within the native valve.

A delivery catheter must often navigate through tortuous anatomy as it is tracked through the vasculature to the treatment site within the heart, to include traversing the aortic arch.

In order that the catheter may be navigated through various anatomical turns as it travels within the vasculature, including the sharp bend of the aortic arch, it is desirable that the clinician have the ability to accurately steer or deflect the catheter as it is guided and advanced to the treatment site. Typical mechanisms for catheter deflection employ a pull wire or wires connected to a distal portion of the catheter and controlled at a proximally located handle. With such mechanisms, when a wire is pulled, the catheter is deflected in the direction of the pulled wire. Although these pull wire mechanisms may work effectively, they add additional components and complexity to the catheter, as well as may increase an already comparatively large profile of a prosthetic heart valve delivery system. Accordingly, a need exists for improved steering mechanisms for a prosthetic heart valve delivery system that can accurately, safely, and successfully achieve deflection of a delivery catheter as it navigates the anatomy of the vasculature while advancing to a desired treatment site without adding additional components, complexity and/or profile to the catheter.

BRIEF SUMMARY OF THE INVENTION

The present invention is directed to overcoming shortcomings and deficiencies of prior art delivery systems by providing prosthetic valve delivery systems with improved deflection capabilities. Such delivery systems employ a compressive force to achieve catheter deflection.

In one aspect of the present invention, a catheter is provided that includes a sheath component having a distal edge and a tip disposed distal of the sheath component, the tip having a proximally-extending projection, wherein when the sheath component is distally advanced against the tip, the distal edge of the sheath component engages the proximally-extending projection of the tip causing deflection of at least a portion of the catheter In accordance with another aspect, a catheter is provided that includes an elongate tubular component with a capsule segment forming a distal portion thereof, the capsule segment being configured for holding a prosthesis in a compressed configuration therein and an inner component that slidably extends within the elongate tubular component, the inner component having a prosthesis retainer that is disposed within the capsule segment, the prosthesis retainer having a proximally-extending projection, wherein when the elongate tubular component is distally advanced relative to the inner component, the capsule segment engages with the proximally-extending projection of the prosthesis retainer causing deflection of at least a portion of the catheter.

In accordance with yet another aspect of the invention, a catheter is provided that includes a sheath component having a distal edge and a tip disposed distal of the sheath component, the tip having a first portion formed from a compressible material and a second portion formed from an incompressible material, wherein when the sheath component is distally advanced against the tip, the first portion of the tip compresses while the second portion retains its shape to thereby cause deflection of at least a portion of the catheter.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a sectional view of a delivery catheter in a delivery configuration in accordance with an embodiment hereof.

FIG. 2 depicts the delivery catheter of FIG. 1 in a deployment configuration with a prosthetic heart valve in a partially deployed configuration.

FIG. 3 depicts the delivery catheter of FIG. 1 in a recapture configuration with the partially deployed prosthetic heart valve, as depicted in FIG. 2, being recaptured and compressed in accordance with an embodiment hereof.

FIG. 6 is an enlarged side view of a distal portion of the delivery catheter in FIG. 1 in accordance with an embodiment hereof.

FIG. 6A is a cross-sectional view of the delivery catheter distal portion shown in FIG. 6 taken along line A-A thereof.

FIG. 6B is a proximal end view of a distal tip of the delivery catheter of FIG. 6 shown removed from the remainder of the delivery catheter for illustrative purposes.

FIG. 7A is a side view of a reinforcement structure in accordance with another embodiment hereof removed from a capsule segment of the delivery catheter of FIG. 6 for illustrative purposes.

FIG. 7B is a side view of the reinforcement structure of FIG. 7A in a deflected state.

FIG. 8C is a side view of the distal portion of the delivery catheter shown in FIG. 8 upon deflection with a compressive force in accordance with an embodiment hereof.

FIG. 9 is a sectional view of a distal portion of a delivery catheter in accordance with another embodiment hereof.

FIGS. 9C and 9D are sectional views of a distal portion of a delivery catheter in accordance with another embodiment hereof.

DETAILED DESCRIPTION OF THE INVENTION

Figure 4A:
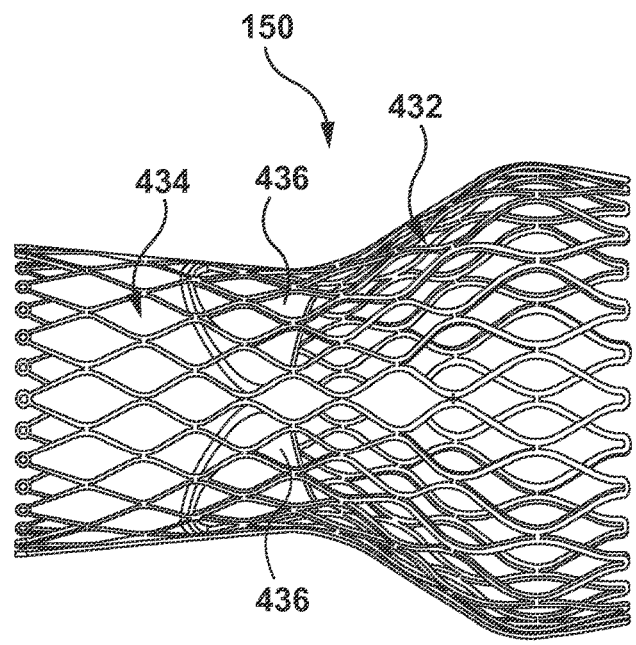
FIG. 4A is a side view of a prosthetic heart valve useful with systems and methods hereof and in a normal, expanded arrangement.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of heart valves, the invention may also be used where it is deemed useful in procedures in the coronary or peripheral vessels. Furthermore, there is no intention to be bound by any expressed or implied theory presented in the preceding technical field, background, brief summary or the following detailed description.

FIGS. 1-3 illustrate in simplified form a delivery catheter 100 in accordance with an embodiment hereof that is configured for endoluminal transcatheter repair/replacement of a defective heart valve. Delivery catheter 100 is depicted in a delivery configuration in FIG. 1 with an exemplary prosthetic heart valve 150 loaded within a distal capsule segment 102 of a tubular sheath component 104. In general terms, prosthetic heart valve 150 includes a stent frame maintaining a valve structure (tissue or synthetic) within the stent frame and having a normal, expanded arrangement and being collapsible to a compressed delivery arrangement for loading within delivery catheter 100. The stent frame is constructed to self-deploy or self-expand when released from delivery catheter 100. In an embodiment, a prosthetic heart valve useful with embodiments hereof can be a prosthetic heart valve as disclosed in U.S. Pat. Appl. Pub. No. 2008/0071361 to Tuval et al., which is incorporated by reference herein in its entirety. Other non-limiting examples of transcatheter heart valve prostheses that may be adapted for use with systems and methods hereof are described in U.S. Pat. Appl. Pub. No. 2006/0265056 to Nguyen et al., U.S. Pat. Appl. Pub. No. 2007/0239266 to Birdsall, and U.S. Pat. Appl. Pub. No. 2007/0239269 to Dolan et al., each of which is incorporated by reference herein in its entirety, and in FIGS. 4A and 4B, described in more detail below.

In the delivery configuration of FIG. 1, distal capsule segment 102 is disposed over prosthetic heart valve 150 to compressively retain the prosthetic heart valve in crimped engagement with a tubular inner shaft or component 106. A flareable funnel segment 108 of distal capsule segment 102 is of a shape memory construction and is distally spaced from prosthetic heart valve 150 in the delivery configuration of FIG. 1. In an embodiment, funnel segment 108 may be of a length in the range of 0.5 cm to 1 cm. After either recapture and/or full deployment of prosthetic heart valve 150, the shape memory property imparted to funnel segment 108 causes the funnel segment to substantially return to a tubular reduced diameter state illustrated in FIG. 1, as more fully described below.

Delivery catheter 100 is depicted in a deployment configuration in FIG. 2 with prosthetic heart valve 150 partially deployed/expanded. Distal capsule segment 102 is shown proximally retracted relative to prosthetic heart valve 150 to permit a distal region 152 of prosthetic heart valve 150 to self-expand. Funnel segment 108 does not resist or impede this expansion but instead is expanded by distal region 152 of prosthetic heart valve 150 to a shape generally corresponding with that of the deploying distal region 152. At this stage of deployment of prosthetic heart valve 150, if a clinician deems the positioning within a native heart valve to be repaired as correct, distal capsule segment 102 is proximally retracted relative to prosthetic heart valve 150 to permit full release and deployment of prosthetic heart valve 150 there from.

When a partial deployment positioning of prosthetic heart valve 150 within the native heart valve is deemed less than optimal, prosthetic heart valve 150 can be resheathed or recaptured within distal capsule segment 102 by distally advancing sheath component 104, as generally depicted in a recapture configuration of delivery catheter 100 shown in FIG. 3. To perform this resheathing/recapture function, funnel segment 108, in the expanded condition, readily slides along an exterior of prosthetic heart valve 150, and effectively serves as a buffer between the structure of the prosthetic heart valve 150 and a stiffer proximal portion of distal capsule segment 102. As distal capsule segment 102 is distally advanced over expanded distal region 152 of prosthetic heart valve 150, the prosthetic heart valve is forcibly compressed back to the initial, compressed delivery configuration depicted in FIG. 1. Due to the shape memory property of funnel segment 108, as funnel segment 108 is maneuvered distal of the collapsing prosthetic heart valve 150, funnel segment 108 substantially returns or self-transitions back to the tubular reduced diameter state depicted in FIG. 1. However, it would be understood by one of ordinary skill in the art that some deformation and/or increase in diameter is likely to have been experienced by at least a distalmost end of funnel segment 108 after resheathing/recapture of the prosthetic heart valve and/or after full deployment thereof.

In general, deployment of prosthetic heart valve 150 is accomplished by proximal movement of sheath component 104 relative to inner shaft 106 and prosthetic heart valve 150 through use of a first actuator mechanism or control 154, with a second actuator mechanism or control 156 being used to provide proximal forces to inner shaft 106 relative to sheath component 104 so as to retract partially expanded prosthetic heart valve 150 into distal capsule segment 102, when recapture is desired. First and second actuator mechanisms 154, 156 are only generally depicted and may take any suitable form for performing the above-noted functions as would be apparent to one of ordinary skill in the art. For instance in an embodiment, each of first and second actuators 154, 156 may be screw-gear mechanisms that are actuated by a clinician. Sheath component 104 and inner shaft 106 are generally thin-walled, flexible tubular structures of a polymeric material, such as polyethylene block amide copolymer, polyvinyl chloride, polyethylene, polyethylene terephthalate, polyamide, or polyimide, and may be formed from one or more tubular components. In embodiments hereof, distal capsule segment 102 and funnel segment 108 may be composite tubular structures of a polymeric material that is reinforced with a braided or webbed layer of a suitable biocompatible metal or metal alloy, such as nitinol, with funnel segment 108 having a nitinol reinforcement layer that permits the funnel segment to be shape set in the shape memory configuration shown in FIG. 1. In other embodiments hereof, prosthesis delivery systems and components thereof as shown and described in U.S Pat. Appl. Pub. No. 2011/0251681 to Shipley et al., U.S. Pat. Appl. Pub. No. 2014/0148889 to Deshmukh et al., U.S. Pat. Appl. Pub. No. 2011/0098804 to Yeung et al., U.S. Pat. Appl. Pub. No. 2012/0310332 to Murray et al., U.S. Pat. Appl. Pub. No. 2012/0305441 to Murray et al., or in U.S Pat. Appl. Pub. No. 2011/0251682 to Murray III et al., each of which is incorporated by reference herein in its entirety, may be adapted for use herein.

Delivery catheter 100 includes an atraumatic distal tip 110 in accordance with an embodiment hereof that has a distally tapering outer surface or profile as would be understood by one of ordinary skill in the art. Distal tip 110 is attached at a distal end of inner shaft 106 to engage or contact with a distal opening 109 of sheath component 104 when delivery catheter 100 is in a delivery configuration, which includes during initial tracking of delivery catheter 100 to a treatment site, after recapture of prosthetic heart valve 150 and during subsequent repositioning of delivery catheter 100, and during removal of delivery catheter 100 from the vasculature at the completion of the interventional procedure. Distal tip 110 is disengaged from distal opening 109 of sheath component 104 during partial and/or full deployment of prosthetic heart valve 150 when delivery catheter 100 is in a deployment configuration. In embodiments hereof, distal tip 110 is secured to inner shaft 106 by means such as gluing, welding and over-molding, such as by injection molding.

As referred to herein, stented transcatheter prosthetic heart valves useful with and/or as part of the various systems, devices, and methods described herein may assume a wide variety of different configurations, such as a bioprosthetic heart valve having tissue leaflets or a synthetic heart valve having polymeric, metallic, or tissue-engineered leaflets, and can be specifically configured for replacing any heart valve. The leaflets can be formed from a variety of materials, such as autologous tissue, xenograph material, or synthetics as are known in the art. Alternatively, the leaflets may be provided as a homogenous, biological valve structure, such as porcine, bovine, or equine valves. Thus, the stented prosthetic heart valve useful with the systems, devices, and methods described herein can be generally used for replacement of a native aortic, mitral, pulmonic, or tricuspid valve, for use as a venous valve, or to replace a failed bioprosthesis, such as in the area of an aortic valve or mitral valve, for example.

In general terms, stented prosthetic heart valves include a tubular stent frame or support structure maintaining a valve structure (tissue or synthetic), with the stent frame having a normal, expanded arrangement and collapsible to a compressed arrangement for loading within a delivery device. The stent frame is normally constructed to self-deploy or self-expand when released from the delivery device. For instance a stent frame suitable for use in embodiments hereof can be formed from a shape memory material such as a nickel titanium alloy (e.g., Nitinol™). With this material, the stent frame is self-expandable from the compressed arrangement to the normal, expanded arrangement, such as by removal of a sheath component of the delivery device. An example of a stented prosthetic heart valve that can be adapted for use in embodiments hereof is a prosthetic heart valve sold under the trade name CoreValve® available from Medtronic CoreValve, LLC. Other non-limiting examples of transcatheter heart valve prostheses useful with systems, devices, and methods hereof are described in U.S. Pat. Appl. Pub. Nos. 2006/0265056; 2007/0239266; and 2007/0239269, the teachings of which were previously incorporated by reference herein.

With the above understanding in mind, one non-limiting example of the stented prosthetic heart valve 150 useful with systems, devices, and methods described herein is illustrated in FIG. 4A. As a point of reference, the prosthetic heart valve 150 is shown in a normal or expanded arrangement in the view of FIG. 4A and is shown in a compressed, delivery arrangement in FIG. 4B, such as when compressively retained within distal capsule segment 102 of sheath component 104. The prosthetic heart valve 150 includes a stent frame or support structure 432 and a valve structure 434. The stent frame 432 can assume any of the forms described above, and is generally constructed so as to be self-expandable from the compressed, delivery arrangement (FIG. 4B) to the normal, expanded arrangement (FIG. 4A). In other embodiments, the stent frame 432 is expandable to the expanded arrangement by a separate device, e.g., a balloon internally located within the stent frame 432. The valve structure 434 is assembled to the stent frame 432 and provides two or more (typically three) leaflets 436. The valve structure 434 can assume any of the forms described above, and can be assembled to the stent frame 432 in various manners, such as by sewing the valve structure 434 to one or more of the wire segments defined by the stent frame 432.

Figure 4B:
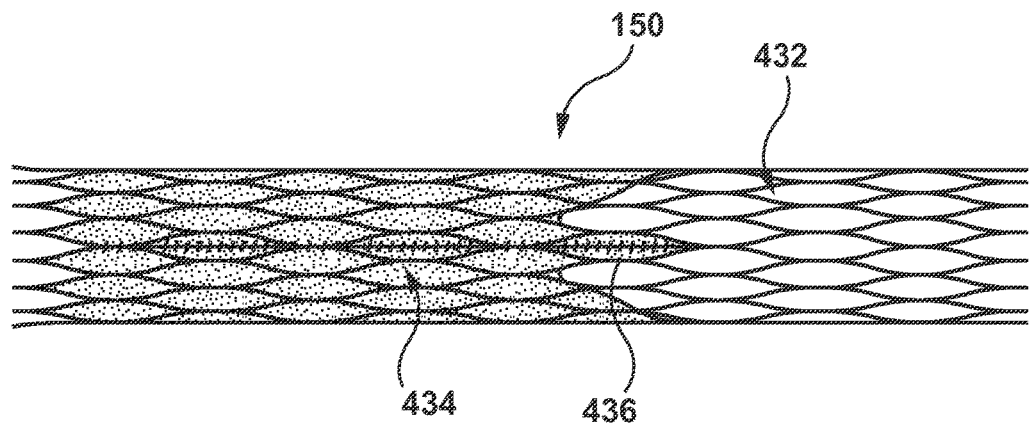
FIG. 4B is a side view of the prosthetic heart valve of FIG. 4A in a compressed arrangement.

With the embodiment of FIGS. 4A and 4B illustrating but one acceptable construction, the prosthetic heart valve 150 is configured for replacing or repairing an aortic valve. Alternatively, other shapes are also envisioned, adapted to the specific anatomy of the native valve to be repaired (e.g., stented prosthetic heart valves in accordance with the present disclosure can be shaped and/or sized for replacing a native mitral, pulmonic, or tricuspid valve). With the one construction of FIGS. 4A and 4B, the valve structure 434 extends less than the entire length of the stent frame 432, but in other embodiments can extend along an entirety, or a near entirety, of a length of the stent frame 432. A wide variety of other constructions are also acceptable and within the scope hereof. For example, the stent frame 432 can have a more cylindrical shape in the normal, expanded arrangement.

Figure 5:
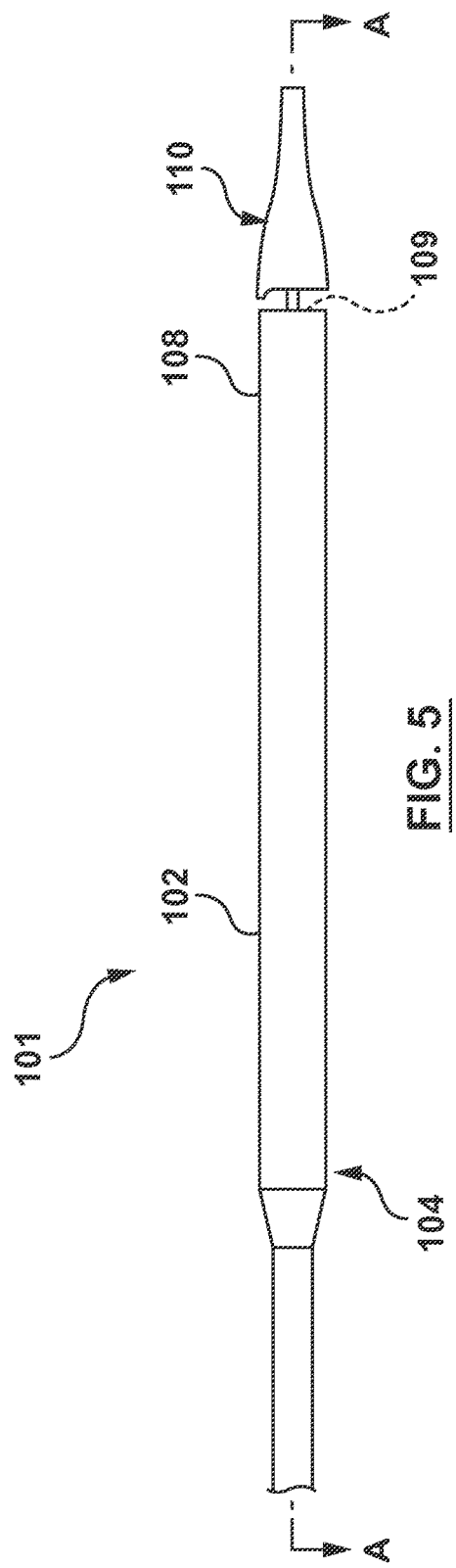
FIG. 5 is an enlarged view of a distal portion of the delivery catheter of FIG. 1 in accordance with an embodiment hereof.
Figure 5A:
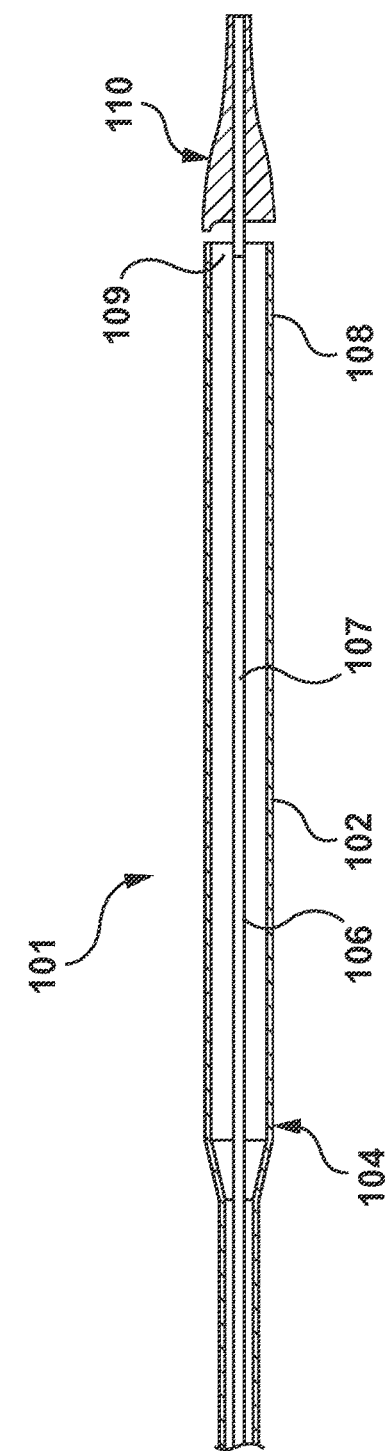
FIG. 5A is a sectional view of the delivery catheter distal portion shown in FIG. 5 taken along line A-A thereof.

With reference to FIGS. 5 and 5A, which are enlarged views of a distal portion 101 of delivery catheter 100 without prosthetic heart valve 150 loaded therein, a guidewire lumen 107 for slidably receiving a guidewire extends through inner shaft 106 and distal tip 110, and a distal opening 109 is defined by funnel segment 108 of distal capsule segment 102. In other embodiments in accordance herewith, distal opening 109 may be defined by a distal end of a capsule segment that does not include a funnel segment or by a distal end of a sheath component that does not include either of a capsule segment or a funnel segment. Relative movement between distal tip 110 and sheath component 104 that is caused by a clinician actuating or manipulating one or both actuation mechanisms 154, 156 will result in the separation of distal tip 110 from distal opening 109 to permit deployment of prosthetic heart valve 150, as would be understood by one of ordinary skill in the art.

As described above, a delivery catheter must often navigate through tortuous anatomy, including traversing the aortic arch, as it is tracked through the vasculature to the desired treatment site within the heart. While the delivery catheter can be generally advanced along a guidewire, it must also be steered or deflected to safely and accurately deliver the prosthesis to its destination. Deflection mechanisms known in the art typically employ a pull wire or wires operably coupled to a distal portion of the delivery catheter, and controlled or manipulated at a proximal end of the delivery system, so that when the wire is pulled, the distal portion of the delivery catheter deflects. Delivery catheters in accordance with embodiments hereof eliminate the need for pullwires and attendant mechanisms associated therewith by using a compressive force between components of the delivery catheter to achieve improved deflection of the catheter.

Figure 6C:
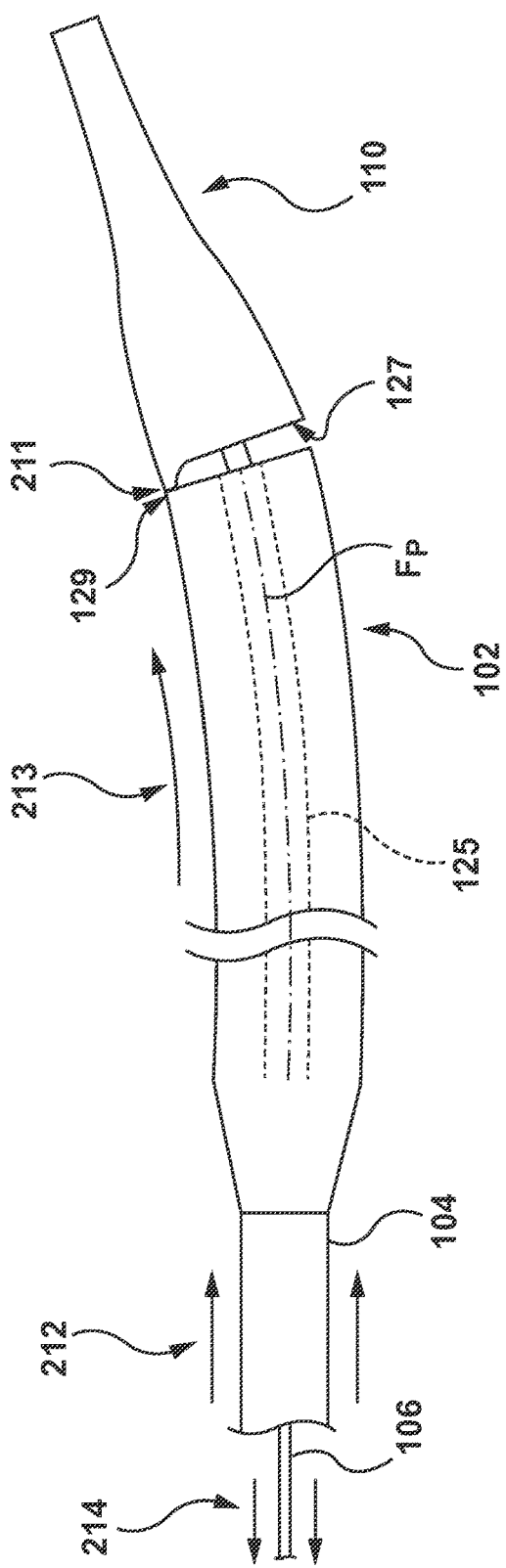
FIG. 6C is an enlarged side view of the distal portion of the delivery catheter shown in FIG. 6 upon deflection with a compressive force in accordance with an embodiment hereof.

FIGS. 6, 6A, 6B and 6c are various views of the distal portion 101 of delivery catheter 100 in accordance with an embodiment hereof. A distal edge 129 defines distal opening 109 of distal capsule segment 102. With reference to FIGS. 6 and 6B, distal tip 110 includes a proximally extending projection 211 that is shown in FIG. 6 distally spaced from an opposing segment of distal edge 129. With reference to FIG. 6C, when sheath component 104 and capsule segment 102 are distally advanced in the direction of arrows 212 against distal tip 110 while a proximal force is applied to distal tip 110 in the direction of arrows 214 via inner shaft 106, distal edge 129 engages proximally extending projection 211, causing deflection in the direction of arrow 213 of at least a distal portion of the catheter. In an embodiment, a compressive force can be applied by a capsule movement mechanism or actuator located in a handle component. In one such embodiment, a capsule movement mechanism or actuator already has the capacity to distally force or compress a capsule segment into a distal tip to overcome typical shaft compression seen on loading a prosthetic heart valve within the capsule segment, known as performing an "overdrive" maneuver by a clinician. The same structures of the delivery catheter and/or use thereof may be suitable to advance the capsule segment 102 into the distal tip 110 such that the proximally extending projection 211 engages with and causes deflection of at least a distal portion of the catheter.

In the embodiment shown in FIG. 6B, a circumferential segment of a proximal end 127 of distal tip 110 forms projection 211, with the circumferential segment proximally extending from or being raised relative to a remaining surface of proximal end 127 of distal tip 110. In various embodiments, the circumferential segment that forms projection 211 may extend around more or less than one third of a circumference of the proximal end 127 of distal tip 110, and may have any suitable shape or size for engaging the distal edge 129 of the capsule segment 102. Distal tip 110 with projection 211 may be formed as a molded component of a polyether block amide (PEBAX), a urethane, silicone, or other elastomeric material or flexible polymeric material, as would be suitable for a distal tip or nosecone as would be understood by one of ordinary skill in the art. In an embodiment, a more rigid material, such as one of a hard plastic and metal, may be overmolded onto a material that forms the remainder of the distal tip 110 to provide a "bump" or projection 211 thereon.

With reference to FIGS. 6, 6A and 6C and in accordance with an embodiment hereof, capsule segment 102 has a tubular shape with a pair of longitudinally-extending supports or spines 125 embedded in a wall thereof, between inner and outer polymeric layers, at diametrically opposed locations, or 180 degrees apart, so that they run in parallel to each other. In such an embodiment, proximally-extending projection 211 of distal tip 110 is positioned to engage distal edge 129 of capsule segment 102 at a point that is substantially midway between the pair of longitudinally-extending supports 125, or stated another way at a point approximately 90 degrees from each of the supports, to permit flexing or deflection of capsule segment 102 along a desired flex plane $F_P$ that extends through the pair of longitudinally-extending supports 125 as shown in FIG. 6A. Accordingly, the capsule segment 102 bends about the flex plane $F_P$ in an "upward" or "downward" direction relative to the positions shown in a comparison of FIGS. 6 and 6C as would be understood by one of skill in the art.

In an embodiment, longitudinally-extending supports 125 of capsule segment 102 are longitudinally-extending and parallel spines formed in a laser cut tube, such as longitudinally-extending spines 725 formed in laser cut tube 780 shown in FIGS. 7A and 7B that are separated and joined by a series of C-shaped segments 782 that have a series of gaps 784 therebetween. A desired flex plane $F_P$ for a capsule segment formed to include laser cut tube 780 extends through the pair of parallel spines 725, as shown in FIG. 7B, and flexing or bending of the capsule segment in an "upward" or "downward" direction (relative to the positions shown in a comparison of FIGS. 7A and 7B) is further accommodated by the flexibility or compressibility imparted by the series of C-shaped segments 782 and gaps 784 to portions of the capsule segment that are 90 degrees displaced from each of the splines 725. In order to form capsule segment 102 or other capsule segments for use in embodiments hereof, laser cut tube 780 is embedded or encapsulated within polymeric layers of suitable material(s) with a flareable distal portion 792 of the laser cut tube 780 lying within funnel segment 108 and with a proximal portion 790 of the laser cut tube 780 lying within a proximal end of capsule segment 102. More particular features of laser cut tubes and constructions and functions of capsule segments that employ such may be found in U.S. Pat. Appl. Pub. No. 2011/00988804, which was previously incorporated by reference herein. For purposes of the present embodiment, FIGS. 7A and 7B illustrate one embodiment of laser cut tube 780 useful with capsule segment 102 of FIGS. 1-3, 5, and 6 and other embodiments described herein, such as, for example, those illustrated in FIGS. 8 and 9. In an embodiment in which laser cut tube 780 is employed, projection 211 of distal tip 110 is aligned to engage distal edge 129 of capsule segment 102 at a point that is substantially midway between the pair of longitudinally-extending splines 725 to facilitate flexing along a desired flex plane $F_P$ that extends through the pair of parallel spines 725, as shown in FIG. 7B. Accordingly, the capsule segment 102 incorporating laser cut tube 780 bends about the flex plane $F_P$ in an "upward" or "downward" direction relative to the positions shown in a comparison of FIGS. 7A and 7B as would be understood by one of skill in the art.

Figure 7C:
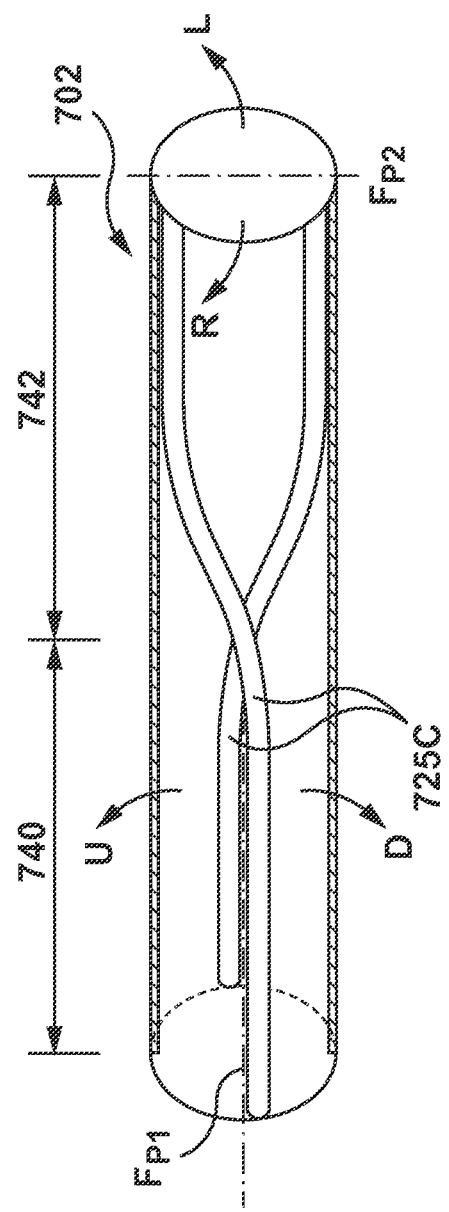
FIG. 7C is a schematic sectional view of a capsule segment in accordance with another embodiment hereof.
Figure 8:
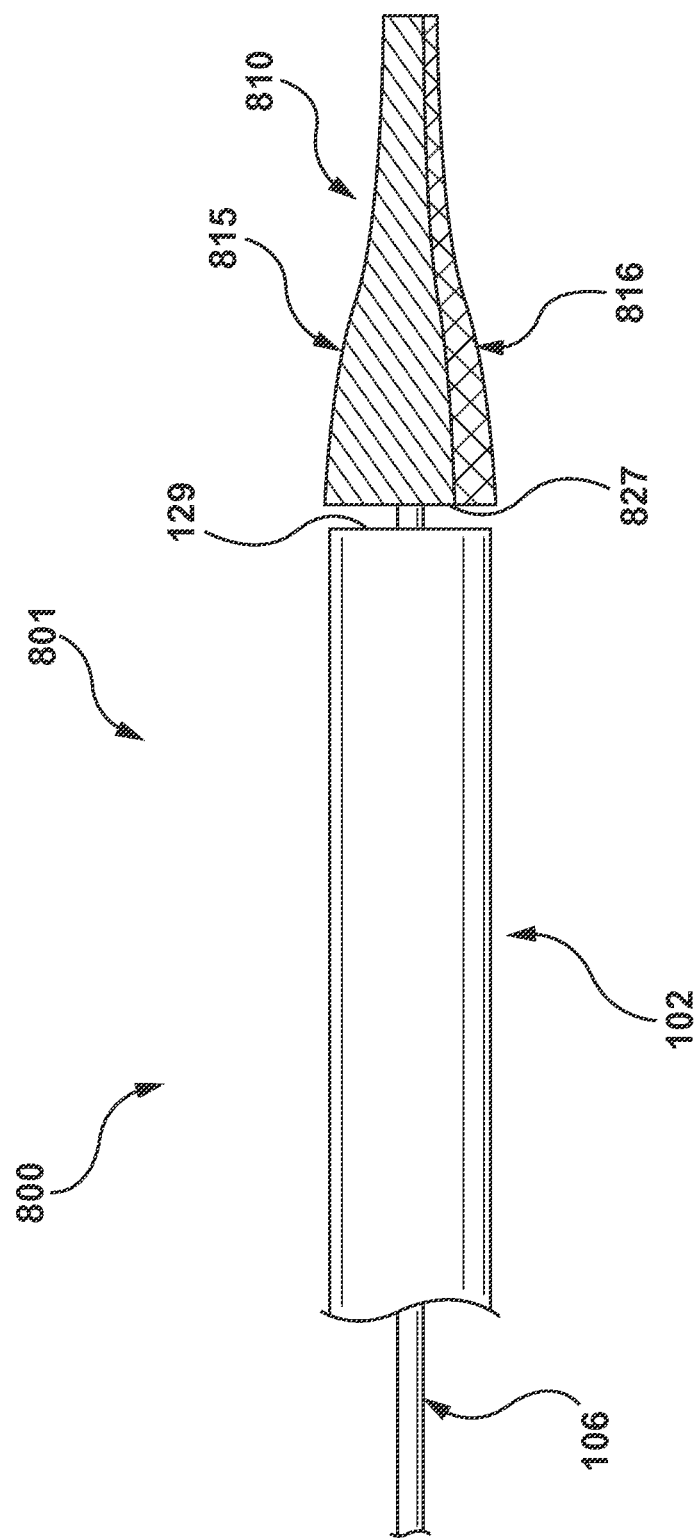
FIG. 8 is an enlarged side view of a distal portion of a delivery catheter in accordance with another embodiment hereof.

In another embodiment, a capsule segment 702 shown in a schematic cross-section in FIG. 7C includes a pair of splines 725C that wrap or curve about a longitudinal axis thereof. More particularly, the pair of splines 725C curve from a first parallel orientation in a proximal portion 740 of the capsule segment 702 to a second parallel orientation that is 90 degrees out of phase from the first parallel orientation in a distal portion 742 of the capsule segment 702 in order to provide the capsule segment with dual or multi axis deflection. In such an embodiment, the proximal portion 740 of the capsule segment 702 will deflect or bend "upward" or "downward" relative to the position shown in FIG. 7C about a first flex plane $F_{P1}$ that extends between the pair of parallel splines 725C, as represented by arrows U and D. In addition in such an embodiment, the distal portion 742 of the capsule segment 702 will deflect or bend "rightward" (out of the page) or "leftward" (into the page) relative to the position shown in FIG. 7C about a second flex plane $F_{P2}$ that extends between the pair of parallel splines 725C, as represented by arrows R and L. In this manner, the capsule segment 702 will deflect along dual axes when compressed or forced against projection 211 of distal tip 110, or when compressed or forced against a distal tip 810 described below. It should be understood that the pair of splines 725C may be a portion of a laser cut tube with additional features, such as a flareable distal portion, and/or a series of alternating C-shaped segments and gaps as described above with reference to laser cut tube 780.

Figure 8B:
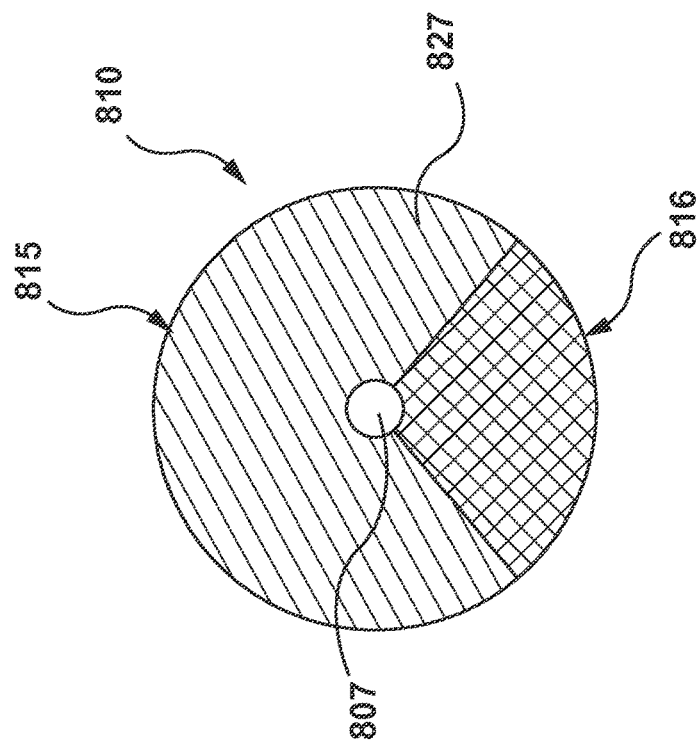
FIG. 8B is a cross-sectional view of the distal tip of FIG. 8A taken along line B-B thereof in accordance with an embodiment hereof.
Figure 8A:
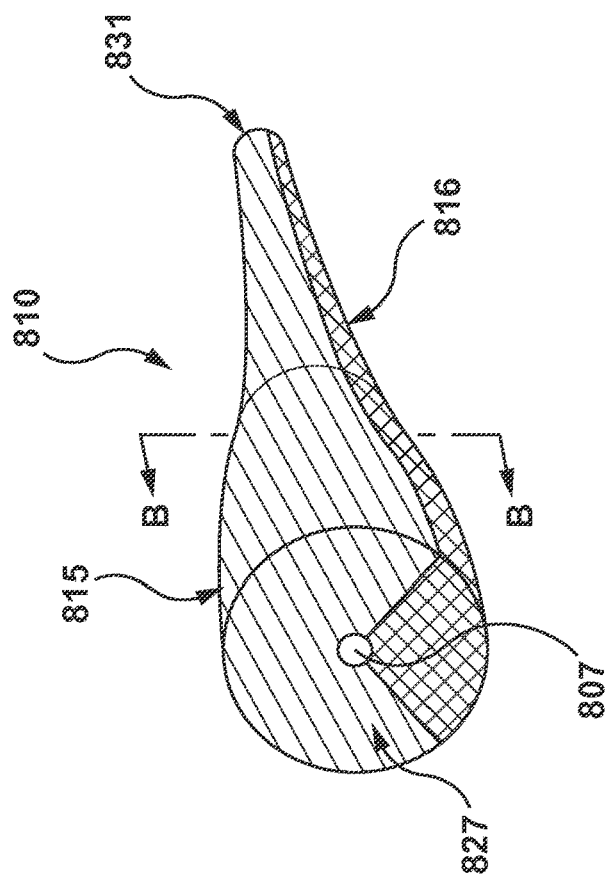
FIG. 8A is a perspective view of a proximal end of a distal tip of the delivery catheter of FIG. 8 shown removed from the remainder of the delivery catheter for illustrative purposes.

FIGS. 8, 8A, 8B and 8C illustrate a distal portion 801 of a delivery catheter 800 in accordance with another embodiment hereof. A distal tip 810 is shown separated from the remainder of the delivery catheter 800 in FIG. 8A with FIG. 8B being a cross-sectional view of distal tip 810 taken along line B-B in FIG. 8A. As in prior embodiments, distal tip 810 includes a guidewire lumen 807 therethrough that is sized to receive a guidewire for tracking delivery catheter 800 within the vasculature and heart structures to a desired treatment site. In the present embodiment, distal tip 810 is formed from two materials, wherein a first material may be considered compressible and wherein a second material may be considered incompressible. With reference to FIGS. 8A and 8B, a longitudinally-extending first portion 815 of distal tip 810 is formed from a compressible first material that may be considered soft and deformable, and a longitudinally-extending second portion 816 of distal tip 810 is formed from an incompressible second material that may be considered hard and/or rigid. In embodiments hereof, the compressible or soft and deformable first material may be low durometer polyether block amide (PEBAX), such as 35D PEBAX, and the incompressible or hard and rigid second material may be high durometer PEBAX, such as 70D PEBAX. In another embodiment, the compressible or deformable longitudinally-extending first portion 815 of distal tip 810 may be formed from a material such as ChronoPrene™ 15A or 75A available from AdvanSource Biomaterials Corp. of Wilmington, Mass. In an embodiment, first portion 815 and second portion 816 of distal tip 810 may be considered to form first and second longitudinally-extending sections 815, 816, respectively, wherein each section 815, 816 distally tapers from a proximal end 827 to a distal end 831 of distal tip 810 to provide an atraumatic profile thereto. As well first and second longitudinally-extending sections 815, 816 have proximal-facing surfaces that form proximal end 827 and have distal-facing surfaces that form distal end 831. In an embodiment, the first longitudinally-extending section 815 comprises more than 50% of the material that forms distal tip 810. In an embodiment, distal tip 810 may be formed as a molded component with first portion 815 being overmolded onto second portion 816.

In accordance with embodiments hereof, distal tip 810 is connected to inner shaft 106 and is disposed distal of sheath component 104 and, more particularly, distal capsule segment 102 thereof. When sheath component 104 and capsule segment 102 are distally advanced in the direction of arrow 812 against distal tip 810, while a proximal force is applied to distal tip 810 in the direction of arrow 814 via inner shaft 106, first portion 815 of distal tip 810 compresses or deforms at a point of contact 817 with the capsule segment, while second portion 816 of distal tip 810 retains its original shape/length, thereby causing deflection of at least distal portion 801 of catheter 800, as shown in FIG. 8C.

Figure 9A:
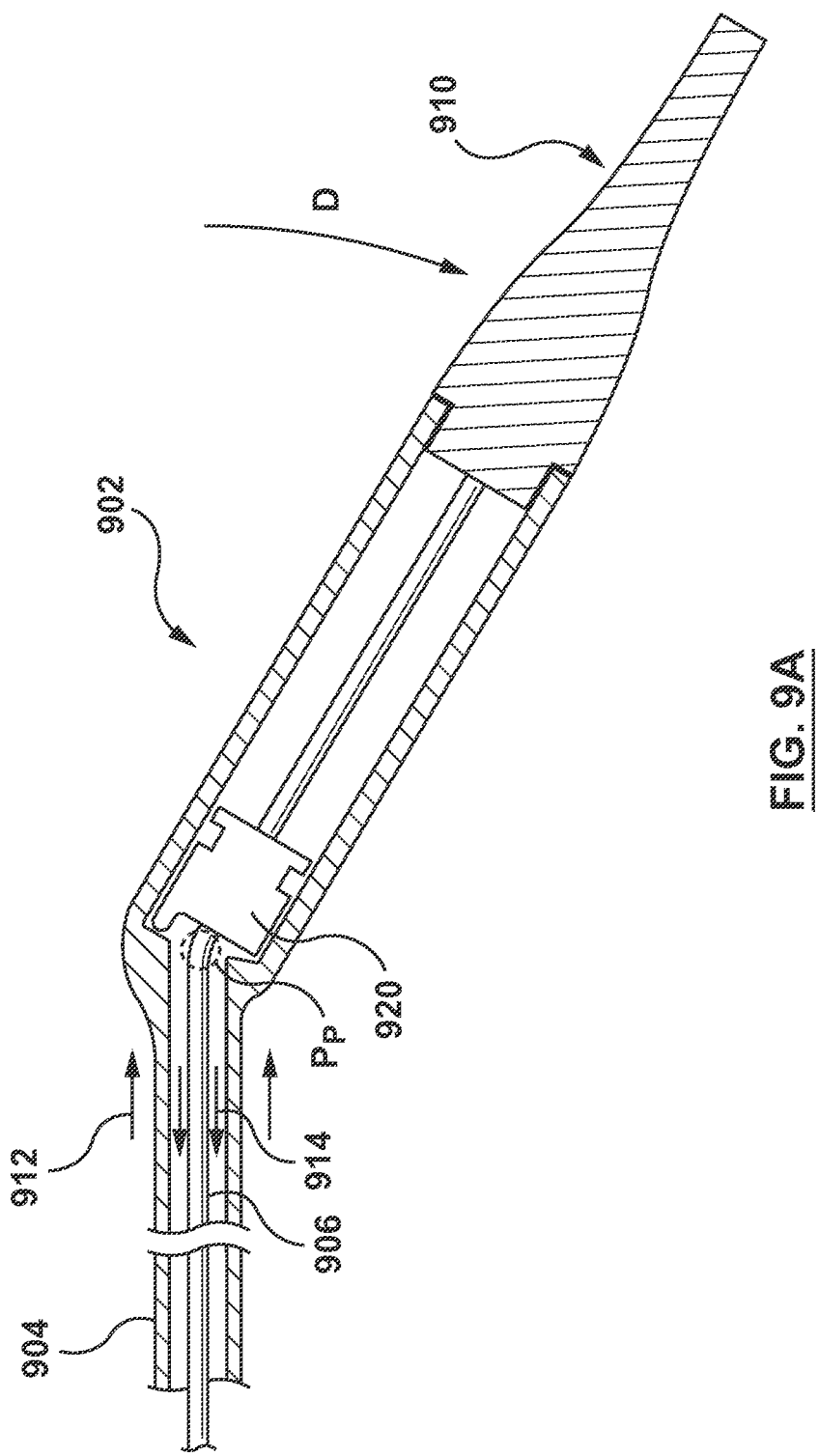
FIG. 9A is a side view of the distal portion of the delivery catheter shown in FIG. 9 upon deflection with a compressive force in accordance with an embodiment hereof.
Figure 9B:
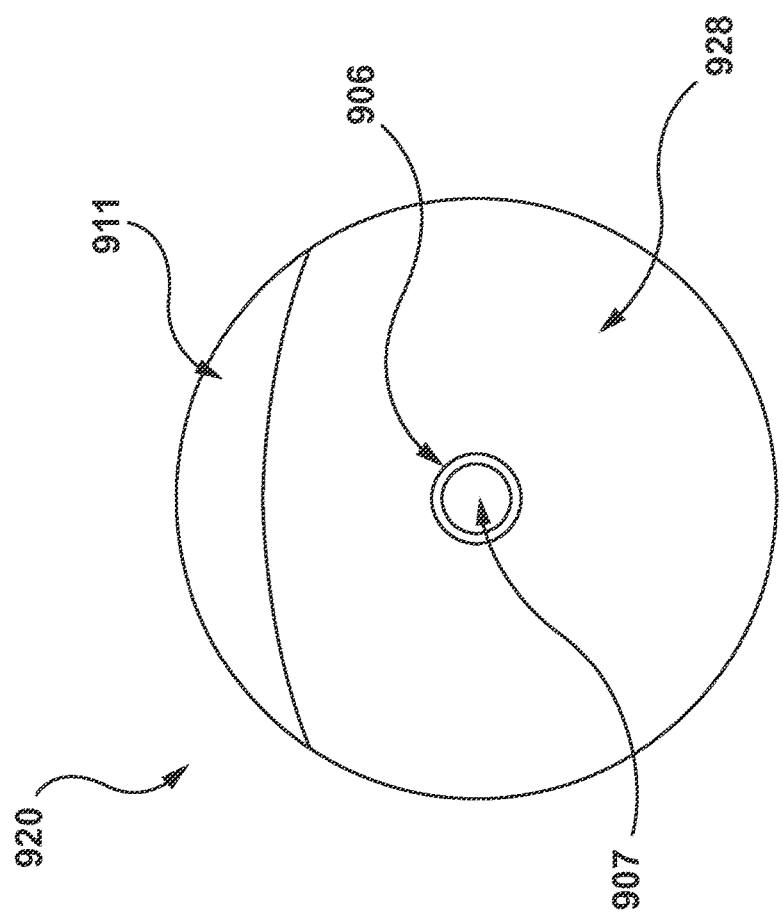
FIG. 9B is a proximal end view of a prosthesis retainer of the delivery catheter of FIG. 9 shown removed from the remainder of the delivery catheter for illustrative purposes.

In another embodiment, with reference to FIGS. 9, 9A, and 9B, a distal portion 901 of a delivery catheter 900 includes an elongate tubular or sheath component 904 with a capsule segment 902 forming a distal end thereof. As described in previous embodiments, capsule segment 902 is configured for holding a prosthetic valve, such as prosthetic heart valve 150 (not shown), in a compressed configuration therein. In the embodiment illustrated in FIG. 9, a tubular inner component 906 slidably extends within the elongate tubular component 904 and includes a prosthesis or valve retainer 920 attached thereto. The prosthesis retainer 920 is a molded component configured for securing a proximal end of the valve prosthesis during loading and delivery of the valve prosthesis, as would be understood by one of skill in the art, and is secured along the inner component 904 to be disposed within the capsule segment 902 as shown in FIG. 9. In accordance with an embodiment hereof, the prosthesis retainer 920 includes a proximally-extending projection 911, as shown in FIG. 9B and explained in more detail below. An atraumatic distal tip 910 is attached to a distal end of the inner component 906 to mate with a distal edge 929 of the capsule segment 902, wherein the prosthesis retainer 920 is proximally spaced from the distal tip 910.

When the elongate tubular component 904 is distally advanced in the direction of arrow 912, the capsule segment 902 engages with the proximally-extending projection 911 of the prosthesis retainer 920, causing deflection of at least the distal portion 901 of the delivery catheter 900 about a pivot point $P_P$, as shown in FIG. 9A. In an embodiment, when the elongate tubular component 904 is distally advanced relative to the inner component 906, an opposing distally-facing inner surface 921 of the capsule segment 902 engages with the proximally-extending projection 911. In such an embodiment, when the delivery catheter 900 is in a delivery configuration the prosthesis retainer 920 may be considered spaced from the distally-facing inner surface 921 of the capsule segment 902 by the projection 911. In an embodiment, the projection 911 is a circumferential segment of a proximal end of the prosthesis retainer 920 that extends from a remainder thereof. In the embodiment shown in FIG. 9B, a proximal end 928 of the prosthesis retainer 920 forms the projection 911, with the circumferential segment proximally extending from or being raised relative to a remaining surface of the proximal end 928 of the prosthesis retainer 920. In various embodiments, the circumferential segment that forms the projection 911 may extend around more or less than one third of the circumference of the proximal end 928 of the prosthesis retainer 920, and may have any suitable shape or size for engaging the distally-facing inner surface 921 of the capsule segment 902.

In another embodiment shown in FIGS. 9C and 9D, a prosthesis retainer 920C permits a clinician to select or change a direction of deflection for the distal portion 901 of the delivery catheter 900. Prosthesis retainer 920 includes an inner member 955 that is rotatably coupled to an outer member 957. The outer member 957 is secured to the inner component 906 of the delivery catheter 900, while the inner member 955 having a projection 911C is attached to a tubular shaft 905 that extends proximally within elongate tubular component 904 to be operably coupled to a handle component (not shown) of the delivery catheter 900. Tubular shaft 905 is configured to be rotated about a longitudinal axis of the delivery catheter 900 so as to concurrently rotate the inner member 955 of the prosthesis retainer 920C relative to elongate tubular component 904, and more particularly to rotate the projection 911C of the inner member 955 relative to the capsule segment 902 thereof. In this manner, projection 911C may be repositioned to act against distally-facing inner surface 921 of the capsule segment 902 at various contact points to permit a change in a direction of deflection. For instance, projection 911C may act against a contact point $C_{P1}$, as shown in FIG. 9C, to deflect or bend the distal portion 901 in the direction of arrow $D_1$, or projection 911C may be rotated to act against a contact point $C_{P2}$, as shown in FIG. 9D, to deflect or bend the distal portion 901 in the direction of arrow $D_2$, which results in a direction of defection that is 180 degrees from the direction of deflection in FIG. 9C.

In embodiments in accordance herewith, a guidewire lumen 907 for slidably receiving a guidewire extends through the inner component 906, the prosthesis retainer 920, and the distal tip 910. In another embodiment hereof, the distal tip 910 forcibly interacts with the distal opening 909 to be retained by the distal opening 909 when the delivery catheter 900 is in the delivery configuration. Retained by the distal opening 909 means that the distal tip 910 is forcibly secured or held within the distal opening 909 such that during tracking of the delivery catheter 900 through the anatomy of the patient, unintentional or inadvertent, longitudinal separation of the distal tip 910 from the capsule segment 902 is prevented. In other words, a longitudinal position of the distal tip 910 relative to the distal opening 909 is maintained when the delivery catheter 900 is in the delivery configuration. In such an arrangement, a proximal a shelf segment 932 of the distal tip 910 continually radially supports the distal opening 909 during advancement of the delivery catheter 900 through the vasculature and structures of the heart. In an embodiment, an interference or tight plug-like compression fit of the distal tip 910 within the distal opening 909 permits the distal tip 910 to be retained by the distal opening 909. In an embodiment in accordance with FIG. 9, the distal tip 910 includes the shelf segment 932 located between a proximal end 927 of the distal tip 910 and a proximally facing abutment surface 933 of the distal tip 910 that forms a radially extending circumferential ridge around the distal tip 910, to facilitate the interference or tight plug-like compression fit of the distal tip 910 within the distal opening 909 of the capsule segment 902. Other non-limiting examples of distal tip and capsule segment or sheath component engagements that may be useful with systems, devices, and methods hereof are described in U.S. Pat. Appl. Pub. No. 2014/0148889, the teaching of which was previously incorporated by reference herein.

In accordance with embodiments hereof, elongate tubular component 904, capsule segment 902, inner component 906 and distal tip 910 may be formed of any of the materials and/or constructions noted above for forming tubular sheath component 104, capsule segment 102, inner shaft 106 and distal tip 110. In embodiment hereof, prosthesis retainer 920 may be a molded component formed from a stainless steel, a hard machinable polymer such as a suitable polycarbonate, a polyetheretherketone (PEEK), a hard nylon or a suitable ULTEM polyetherimide (PEI).

Delivery systems with various specific designs and features can be adapted for use with the distal tips, capsule segments and embodiments of the invention as described herein. Descriptions of some such systems and specific features thereof can be found in the various U.S. Patents and Patent Application Publications referred to and incorporated herein. As noted, a prosthetic heart valve can be delivered by delivery systems such as illustrated herein, as such prosthetic heart valves can be designed for replacement of the aortic valve, mitral valve, tricuspid valve, or pulmonary valve by way of a patient's vasculature, such as including access through a patient's femoral artery or femoral vein, or otherwise, as appropriate in accordance with known or developed delivery techniques utilizing percutaneous delivery.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A catheter comprising:
a sheath component having a distal edge; and
a tip disposed distal of the sheath component, the tip having a proximally-extending projection,
wherein the proximally-extending projection longitudinally extends from a remaining surface of a proximal end of the tip, and
wherein when the sheath component is distally advanced against the tip, the distal edge of the sheath component engages the proximally-extending projection of the tip causing deflection of at least a portion of the catheter.

2. The catheter of claim 1, wherein a circumferential segment of the proximal end of the tip forms the projection.

3. The catheter of claim 2, wherein the circumferential segment extends around less than one third of a circumference of the proximal end of the tip.

4. A catheter comprising:
a sheath component having a distal edge; and
a tip disposed distal of the sheath component, the tip having a proximally-extending projection,
wherein when the sheath component is distally advanced against the tip, the distal edge of the sheath component engages the proximally-extending projection of the tip causing deflection of at least a portion of the catheter, and
wherein the sheath component includes a capsule segment configured for holding a prosthesis in a compressed configuration therein, and wherein the capsule segment defines the distal edge of the sheath component.

5. The catheter of claim 4, wherein the capsule segment has a tubular shape with a pair of longitudinally-extending supports embedded in a wall thereof at diametrically opposed locations.

6. The catheter of claim 5, wherein the distal edge of the capsule segment engages with the proximally-extending projection at a point that is midway between the pair of longitudinally-extending supports.

* * * * *